United States Patent
Giron et al.

(10) Patent No.: US 8,563,556 B2
(45) Date of Patent: Oct. 22, 2013

(54) CRYSTALLINE FORMS AND TWO SOLVATED FORMS OF 4-AMINO-5-FLUORO-3-[5-(4-METHYLPIPERAZIN-1-YL)-1H-BENZIMIDAZOL-2-YL] QUINOLIN-2(1H)-ONE LACTIC ACID SALTS

(75) Inventors: Danielle Giron, Mulhouse (FR); Walter Hammerschmidt, Basel (CH); Philippe Piechon, St. Louis (FR); Johanne Polasek, Geneva (CH); Andreas Schreiner, Rheinfelden (CH); Frank Stowasser, Murg (DE)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 12/922,213

(22) PCT Filed: Mar. 18, 2009

(86) PCT No.: PCT/EP2009/053222
§ 371 (c)(1),
(2), (4) Date: Sep. 13, 2010

(87) PCT Pub. No.: WO2009/115562
PCT Pub. Date: Sep. 24, 2009

(65) Prior Publication Data
US 2011/0021536 A1    Jan. 27, 2011

Related U.S. Application Data

(60) Provisional application No. 61/037,746, filed on Mar. 19, 2008.

(51) Int. Cl.
*A61K 31/496* (2006.01)
*C07D 401/14* (2006.01)
*A61P 35/00* (2006.01)
*A61P 35/02* (2006.01)

(52) U.S. Cl.
USPC ...................................... 514/253.07; 544/363

(58) Field of Classification Search
None
See application file for complete search history.

(56) References Cited

U.S. PATENT DOCUMENTS

| 6,774,237 B2 | 8/2004 | Renhowe et al. |
| 2004/0092535 A1 | 5/2004 | Barsanti |
| 2005/0203101 A1 | 9/2005 | Barsanti |
| 2005/0256157 A1 | 11/2005 | Gesner |
| 2005/0261307 A1 | 11/2005 | Cai |
| 2006/0183750 A1* | 8/2006 | Menezes et al. ......... 514/253.07 |

FOREIGN PATENT DOCUMENTS

| WO | 2004043389 A2 | 5/2004 |
| WO | WO2006/127926 | * 11/2006 |
| WO | WO2007/064719 | 6/2007 |
| WO | 2009/115562 A2 | 9/2009 |
| WO | 2009115517 A2 | 9/2009 |

OTHER PUBLICATIONS

Morissette et al. in Drug Delivery Reviews, 56 (2004) 275-30.*
Definition About in www.merriam-webster.com/dictionary/about (retrieved online Jan. 8, 2013).*
Hecht et al. In Journal of Clinical Oncology (Meeting Abstracts) 2005;23.*
Wedge et al. describes in Cancer Research 2002;62:4645-4655.*
International Search Report dated Sep. 24, 2009 for PCT/EP2009/053222.
"Polymorphism in pharmaceutical solids", edited by H.G. Brittain, Marcel Dekker, D.J.W. Grant (chapter1): pp. 1-10; and J.K. Guillory (chapter 5): pp. 183-226 (1999).
Mino R. Caria, "Crystalline polymorphs of Organic Compounds"; Topics in curent chemistry, 1998, vol. 198, pp. 163-208 (D3).
S. Byrnet al., "Pharmaceutical solids: A strategic approach to regulatory considerations", Pharmaceutical Research, 1995, vol. 12(7): 945-954.
Rodriguez-Spong et al, 2004, "General principles of pharmaceutical solid polymorphism: a supramolecular perspective", Advance Drug Delivery Reviews, 56(3):241-274.

* cited by examiner

*Primary Examiner* — Dennis Heyer
(74) *Attorney, Agent, or Firm* — Gregory Ferraro (57) ABSTRACT

Crystalline forms or polymorphs of 4-amino-5-fluoro-3-[5-(4-methylpiperazin-1-yl)-1H-benzimidazol-2-yl]quinolin-2(1H)-one lactic acid salts, as well as to methods of making the same, pharmaceutical compositions comprising the same and methods of treatment using the same.

7 Claims, 10 Drawing Sheets

X-ray Powder Diffraction Peaks of the Anhydrous form II

| ° deg 2 θ | d-space | Relative intensity (%) |
|---|---|---|
| 11.8 | 7.499 | Weak (30) |
| 12.9 | 6.862 | Weak (30) |
| 13.8 | 6.410 | Weak (18) |
| 14.7 | 6.037 | Weak (19) |
| 16.6 | 5.328 | Medium (38) |
| 18.5 | 4.788 | Strong (100) |
| 20.3 | 4.374 | Weak (15) |
| 23.5 | 3.785 | Weak (19) |

Figure 1

X-ray Powder Diffraction Peaks of the hemi-pentahydrate (Peaks between 20-100%)

| ° deg 2 θ | d-space | Relative intensity (%) |
| --- | --- | --- |
| 6.8 | 13.074 | Strong (62) |
| 9.3 | 9.486 | Weak (21) |
| 12.1 | 7.284 | Medium (51) |
| 12.7 | 6.952 | Weak (26) |
| 13.1 | 6.757 | Medium (45) |
| 13.4 | 6.596 | Medium (39) |
| 16.5 | 5.366 | Weak (26) |
| 17.3 | 5.129 | Strong (70) |
| 18.7 | 4.731 | Weak (27) |
| 19.3 | 4.606 | Medium (51) |
| 19.8 | 4.472 | Medium (41) |
| 20.4 | 4.346 | Medium (41) |
| 20.8 | 4.275 | Weak (34) |
| 21.3 | 4.161 | Weak (32) |
| 22.5 | 3.943 | Strong (85) |
| 23.3 | 3.820 | Medium (40) |
| 23.6 | 3.766 | Weak (25) |
| 24.2 | 3.681 | Weak (38) |
| 25.8 | 3.451 | Strong (94) |
| 26.2 | 3.404 | Medium (44) |
| 27.1 | 3.290 | Strong (100) |
| 27.5 | 3.238 | Weak (21) |
| 28.1 | 3.173 | Weak (23) |

Figure 2

X-ray Powder Diffraction Peaks of the Methanol-Solvate (Peaks between 15-100%)

| ° deg 2 θ | d-space | Relative intensity % |
|---|---|---|
| 6.5 | 13.532 | Strong (60) |
| 9.4 | 9.357 | Medium (45) |
| 10.7 | 8.229 | Weak (15) |
| 11.9 | 7.411 | Medium (39) |
| 12.2 | 7.255 | Strong (63) |
| 13.1 | 6.751 | Weak (16) |
| 13.4 | 6.598 | Weak (23) |
| 14.5 | 6.105 | Weak (16) |
| 14.9 | 5.943 | Weak (27) |
| 16.0 | 5.528 | Weak (23) |
| 16.6 | 5.333 | Weak (21) |
| 18.0 | 4.928 | Medium (30) |
| 19.5 | 4.559 | Strong (100) |
| 20.6 | 4.316 | Weak (18) |
| 22.5 | 3.942 | Medium (39) |
| 23.0 | 3.866 | Weak (18)) |
| 23.4 | 3.801 | Medium (37) |
| 24.0 | 3.702 | Strong (82) |
| 26.3 | 3.383 | Strong (58) |
| 27.4 | 3.256 | Weak (25) |
| 27.6 | 3.224 | Weak (19) |
| 29.2 | 3.053 | Medium (42) |

CRYSTALLINE FORMS AND TWO SOLVATED FORMS OF 4-AMINO-5-FLUORO-3-[5-(4-METHYLPIPERAZIN-1-YL)-1H-BENZIMIDAZOL-2-YL]QUINOLIN-2(1H)-ONE LACTIC ACID SALTS

This is a National Stage of International Application No. PCT/EP2009/053222 filed on Mar. 18, 2009, which claims benefit of U.S. Provisional Application No. 61/037,746 filed Mar. 19, 2008, which in its entirety are herein incorporated by reference.

BACKGROUND OF THE INVENTION

1. Field of the Invention

This invention relates to crystalline forms of 4-amino-5-fluoro-3-[5-(4-methylpiperazin-1-yl)-1H-benzimidazol-2-yl]quinolin-2(1H)-one lactic acid salts, as well as to methods of making the same, pharmaceutical compositions comprising the same and methods of treatment using the same.

2. Related Background Art

Polymorphism denotes the existence of more than one crystal structure of a substance. This ability of a chemical substance to crystallize in more than one crystal modification can have a profound effect on the shelf life, solubility, formulation properties, and processing properties of a drug. In addition, the action of a drug can be affected by the polymorphism of the drug molecule. Different polymorphs can have different rates of uptake in the body, leading to lower or higher biological activity than desired. In extreme cases, an undesired polymorph can even show toxicity. The occurrence of an unknown polymorphic form during manufacture can have an enormous impact.

Understanding and controlling polymorphism, then, gives a decided advantage in bringing new drugs to the marketplace. First and foremost, the knowledge of any possible polymorphs for a drug product can be used to diminish the possibility of contamination during a drug's manufacture or storage by other polymorphic forms. Failure to catch contamination can have life-threatening consequences in some cases. Crystallizing an unintended polymorph during manufacture can mean weeks or even months of production downtime while scientists find and correct the cause of the new crystal form or go through another round of testing to obtain approval for the new form.

Second, understanding which crystal structures are possible in some cases allows researchers to maximize the desired properties of a compound such as solubility, formulation properties, processing properties, and shelf life. Understanding these factors early in the development of a new drug may mean a more active, more stable, or more cheaply manufactured drug.

The compound 4-amino-5-fluoro-3-[5-(4-methylpiperazin-1-yl)-1H-benzimidazol-2-yl]quinolin-2(1H)-one has the formula (I):

(I)

as described in U.S. Pat. No. 6,774,237 and WO 2006/127926. WO 2006/127926 provides information of polymorph and solvate forms of 4-amino-5-fluoro-3-[5-(4-methylpiperazin-1-yl)-1H-benzimidazol-2-yl]quinolin-2(1H)-one. WO 2006/127926 does not provide information of the new anhydrous form II, the hemi-pentahydrate form or the methanol-solvate form of 4-amino-5-fluoro-3-[5-(4-methylpiperazin-1-yl)-1H-benzimidazol-2-yl]quinolin-2(1H)-one lactic acid salt of the present invention or the DMF-solvate thereof. Knowledge of the potential polymorphic forms of 4-amino-5-fluoro-3-[5-(4-methylpiperazin-1-yl)-1H-benzimidazol-2-yl]quinolin-2(1H)-one lactic acid salts is useful in the development of a suitable dosage form, because the failure to utilize a single polymorphic form during clinical or stability studies may result in the exact dosage form being used or studied not being comparable from one lot to another. Once chosen, it is important that a polymorphic form can be reproducibly prepared and remain unchanged for prolonged time periods in the dosage form developed. It is also desirable to have a process for producing 4-amino-5-fluoro-3-[5-(4-methylpiperazin-1-yl)-1H-benzimidazol-2-yl]quinolin-2(1H)-one lactic acid salts in high purity since the presence of impurities may produce undesired toxicological effects.

It has now surprisingly been found that the different crystal modifications (novel polymorphic forms or solvated forms) of 4-amino-5-fluoro-3-[5-(4-methylpiperazin-1-yl)-1H-benzimidazol-2-yl]quinolin-2(1H)-one lactic acid salts characterized below can be prepared by choice of specially selected process conditions, e.g., choice of solvent system, duration of crystallization, etc.

SUMMARY OF THE INVENTION

The present invention is directed to substantially pure crystalline forms of an new anhydrous form, a hemi-pentahydrate form, a methanol-solvate form or a DMF-solvate form of 4-amino-5-fluoro-3-[5-(4-methylpiperazin-1-yl)-1H-benzimidazol-2-yl]quinolin-2(1H)-one lactic acid salts.

The invention is further directed to pharmaceutical compositions comprising:
(a) a therapeutically effective amount of a crystalline form of an anhydrous form, a hemi-pentahydrate form, a methanol-solvate form or a DMF-solvate form of 4-amino-5-fluoro-3-[5-(4-methylpiperazin-1-yl)-1H-benzimidazol-2-yl]quinolin-2(1H)-one lactic acid salts thereof of the present invention; and
(b) at least one pharmaceutically acceptable carrier, diluent, vehicle or excipient.

The present invention is also directed to a method of treating a disease which responds to an inhibition of receptor tyrosine kinases as described in U.S. Pat. No. 6,774,237 and WO 2006/127926. These methods include, but are not limited to, inhibition of VEGFR2 and FGFR3 activity comprising the step of administering to a subject in need of such treatment a therapeutically effective amount of a crystalline form of an anhydrous form, a hemi-pentahydrate form or a methanol-solvate form or a DMF-solvate form of 4-amino-5-fluoro-3-[5-(4-methylpiperazin-1-yl)-1H-benzimidazol-2-yl]quinolin-2(1H)-one lactic acid salts thereof of the present invention.

DETAILED DESCRIPTION OF THE INVENTION

The polymorphic form of the anhydrous form of 4-amino-5-fluoro-3-[5-(4-methylpiperazin-1-yl)-1H-benzimidazol-2-yl]quinolin-2(1H)-one lactic acid salt, the polymorphic form of the hemi-pentahydrate form of 4-amino-5-fluoro-3-[5-(4-methylpiperazin-1-yl)-1H-benzimidazol-2-yl]quinolin-2(1H-one lactic acid salt and the methanol-solvate form of 4-amino-5-fluoro-3-[5-(4-methylpiperazin-1-yl)-1H-benzimidazol-2-yl]quinolin-2(1H)-one lactic acid salt can be obtained through transformations of the polymorphs and solvates described in Applicant's pending application WO 2006/127926. These "crystal modifications" (or "polymorphic form(s)", "polymorph(s)", or "crystalline form(s)", as the terms will be used interchangeably herein) differ with respect to thermodynamic stability, physical parameters, x-ray structure and/or preparation processes and differ from the polymorphs and solvates described in WO 2006/127926. The crystalline forms of 4-amino-5-fluoro-3-[5-(4-methylpiperazin-1-yl)-1H-benzimidazol-2-yl]quinolin-2(1H)-one lactic acid salts to which the present invention is directed are characterized by the x-ray powder diffraction patterns shown in FIGS. 1-4.

As used herein, the terms "isolated" and/or "substantially pure" mean more than 50% of the crystalline 4-amino-5-fluoro-3-[5-(4-methylpiperazin-1-yl)-1H-benzimidazol-2-yl]quinolin-2(1H)-one lactic acid salts thereof is present in one of the forms described herein and preferably at least 70%, more preferably at least 80%, and most preferably at least 90% of one of the crystalline forms described herein is present.

Figure 1:
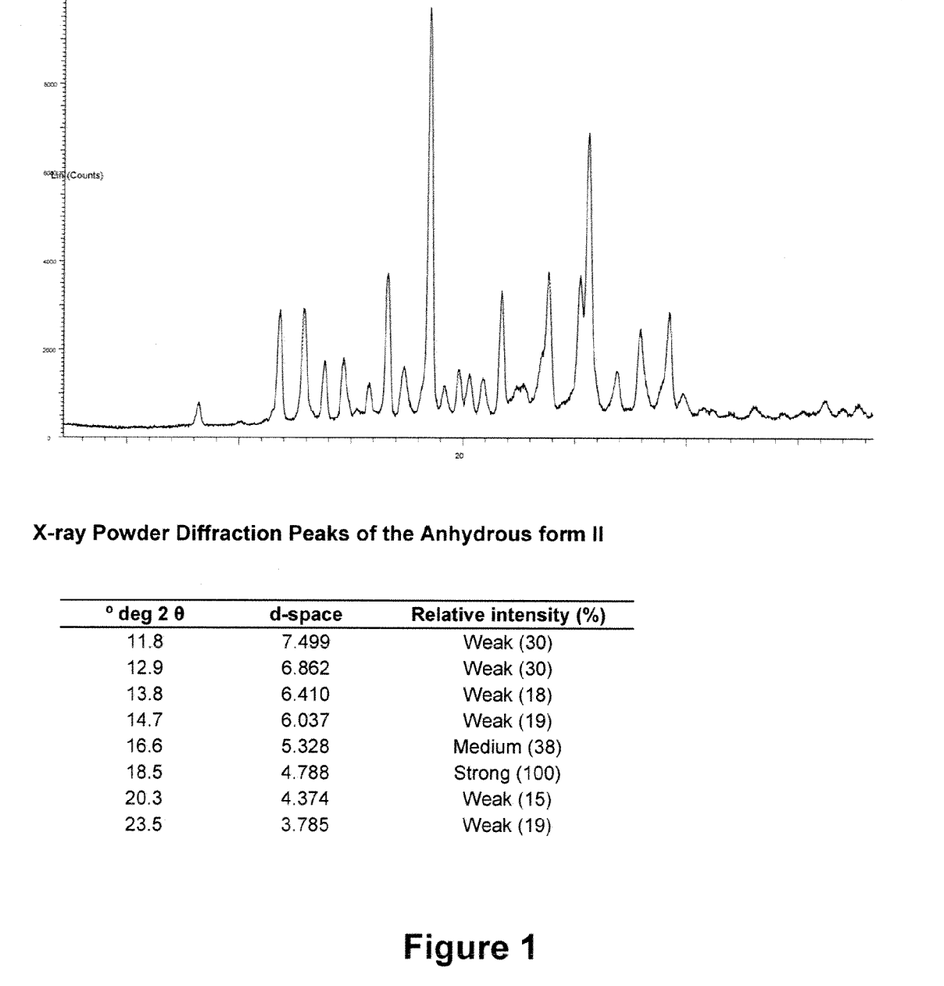
FIG. 1 shows the x-ray powder diffraction patterns for the new anhydrous form of the lactic acid salt of 4-amino-5-fluoro-3-[5-(4-methylpiperazin-1-yl)-1H-benzimidazol-2-yl]quinolin-2(1H)-one.

The first embodiment of the present invention is directed to a substantially pure polymorphic anhydrous form of 4-amino-5-fluoro-3-[5-(4-methylpiperazin-1-yl)-1H-benzimidazol-2-yl]quinolin-2(1H)-one lactic acid salt as shown in FIG. 1. The anhydrous form of the present invention, herein known as anhydrous form II can be isolated from ethanol, ethanol/acetonitrile (98:2) or isopropanol using the polymorph form A described in Applicant's pending application WO 2006/127926. Anhydrous form II can also be isolated from ethanol, acetonitrile, or isopropanol using the form B (monohydrate) described in Applicant's pending application WO 2006/127926.

Figure 2:
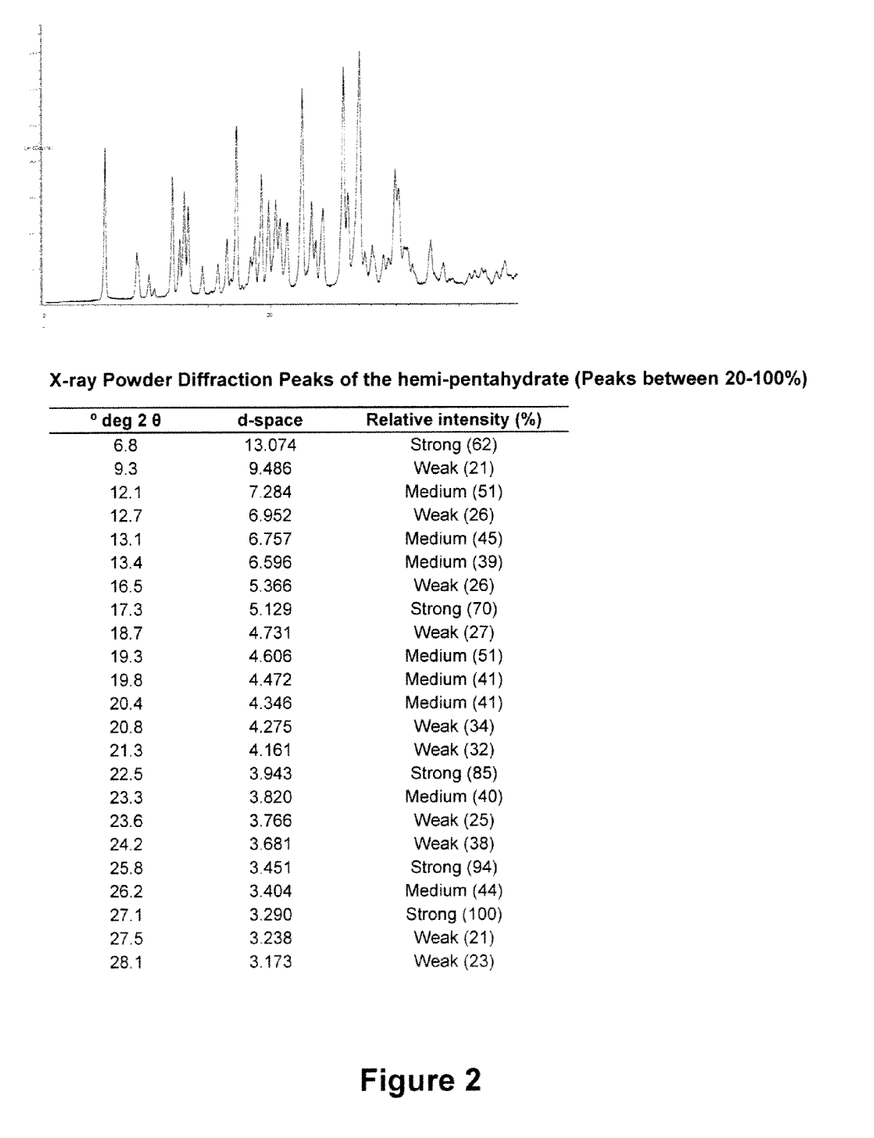
FIG. 2 shows the x-ray powder diffraction patterns for the hemi-pentahydrate form of the lactic acid salt of 4-amino-5-fluoro-3-[5-(4-methylpiperazin-1-yl)-1H-benzimidazol-2-yl]quinolin-2(1H)-one.

The second embodiment of the present invention is directed to a substantially pure polymorphic hemi-pentahydrate form of 4-amino-5-fluoro-3-[5-(4-methylpiperazin-1-yl)-1H-benzimidazol-2-yl]quinolin-2(1H)-one lactic acid salt as shown in FIG. 2. The hemi-pentahydrate form of the present invention can be isolated through crystallization in ethanol/water mixtures. The hemi-pentahydrate form can also be isolated from ethanol/water mixtures (from about 80:20 to about 60:40) or from ethanol/water/tetrahydrofuran mixtures or acetone/water mixtures using the polymorph form A described in Applicant's pending application WO 2006/127926.

Figure 3:
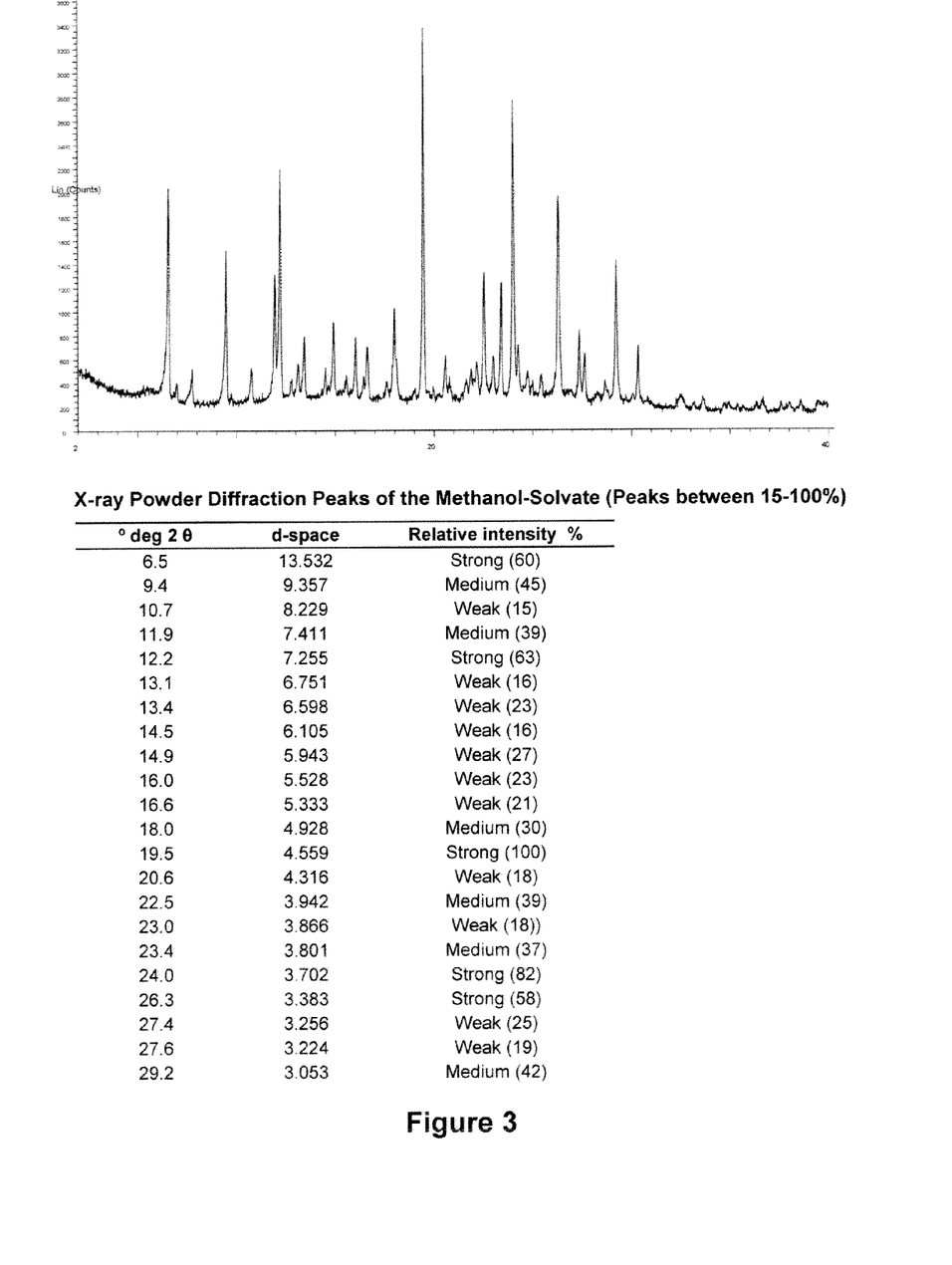
FIG. 3 shows the x-ray powder diffraction patterns for the methanol-solvate form of the lactic acid salt of 4-amino-5-fluoro-3-[5-(4-methylpiperazin-1-yl)-1H-benzimidazol-2-yl]quinolin-2(1H)-one.
Figure 4:
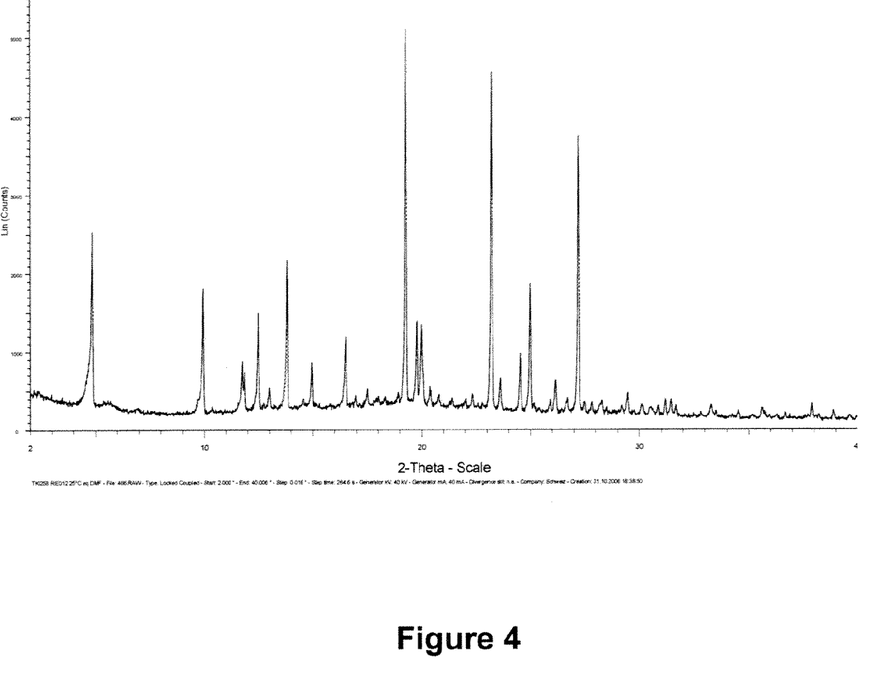
FIG. 4 shows the x-ray powder diffraction patterns for the DMF-solvate form of the lactic acid salt of 4-amino-5-fluoro-3-[5-(4-methylpiperazin-1-yl)-1H-benzimidazol-2-yl]quinolin-2(1H)-one.

The third embodiment of the present invention is directed to a substantially pure polymorphic methanol-solvate form of 4-amino-5-fluoro-3-[5-(4-methylpiperazin-1-yl)-1H-benzimidazol-2-yl]quinolin-2(1H)-one lactic acid salt as shown in FIG. 3.

Various methods can be used to achieve polymorphic forms of the above-noted salts of 4-amino-5-fluoro-3-[5-(4-methylpiperazin-1-yl)-1H-benzimidazol-2-yl]quinolin-2(1H)-one lactic acid salt. Such methods are set forth in the below-presented examples.

Another embodiment of the present invention is directed to a pharmaceutical composition comprising:
(a) a therapeutically effective amount of a substantially pure crystalline forms of 4-amino-5-fluoro-3-[5-(4-methylpiperazin-1-yl)-1H-benzimidazol-2-yl]quinolin-2(1H)-one lactic acid salts characterized by one of the XRPD patterns shown in FIGS. 1-4; and
(b) at least one pharmaceutically acceptable carrier, diluent, vehicle or excipient.

Preferably, more than 50% of the crystalline form present in the composition is of one of the selected forms.

A "therapeutically effective amount" is intended to mean the amount of the inventive polymorph that, when administered to a subject in need thereof, is sufficient to effect treatment for disease conditions alleviated by the inhibition of VEGFR2 and FGFR3 activity. The amount of a given compound of the invention that will be therapeutically effective will vary depending upon factors such as the disease condition and the severity thereof, the identity of the subject in need thereof, etc., which amount may be routinely determined by artisans of ordinary skill in the art.

The at least one pharmaceutically acceptable carrier, diluent, vehicle or excipient including but not limited to microcrystalline cellulose, lactose, dibasic calcium phosphate, tribasic calcium phosphate, sodium starch glycolate (NaSG), crospovidone, crosscarmellose (CC), sodium lauryl sulfate (SLS), Tween, polyethylene glycol (PEG), povidone, hydroxypropyl cellulose (HPMC). Mg stearate, Ca stearate, stearic acid, sodium stearate fumarate and silicon dioxide can readily be selected by one of ordinary skill in the art and will be determined by the desired mode of administration. Illustrative examples of suitable modes of administration include oral, nasal, parenteral, topical, transdermal and rectal. The pharmaceutical compositions of this invention may take any pharmaceutical form recognizable to the skilled artisan as being suitable. Suitable pharmaceutical forms include solid, semisolid, liquid, or lyophilized formulations, such as tablets, powders, capsules, suppositories, suspensions, liposomes and aerosols.

Yet another embodiment of the present invention is directed to a method of treating a disease which responds to an inhibition of VEGFR2 and FGFR3 activity comprising the step of administering to a subject in need of such treatment a therapeutically effective amount of a substantially pure crystalline form of 4-amino-5-fluoro-3-[5-(4-methylpiperazin-1-yl)-1H-benzimidazol-2-yl]quinolin-2(1H)-one lactic acid salt characterized by one of the XRPD patterns shown in FIGS. 1-4.

Diseases which respond to an inhibition of VEGFR2 and FGFR3 activity include but are not limited to diseases such as prostate cancer, colorectal cancer, breast cancer, multiple myeloma, pancreatic cancer, small cell carcinoma, acute myelogenous leukemia, chronic myelogenous leukemia, myelo-proliferative disease, nonsmall cell leukemia, small cell leukemia, chronic lymphoid leukemia, sarcoma, melanoma, lymphoma, thyroid cancer, neuroendocrine cancer, renal cell cancer, gastric cancer, gastrointestinal stromal cancer, glioma, brain cancer, bladder cancer or cholangiocarcinoma. Further indications are described in Applicant's patents and/or U.S. Pat. No. 6,774,237, U.S. patent Ser. Nos. 10/644,055, 10/983,174, 10/839,793, 11/041,191 and WO 2006/127926.

As noted above, illustrative modes of administration include oral, nasal, parenteral, topical, transdermal and rectal. Administration of the crystalline forms may be accomplished by administration of a pharmaceutical composition of this invention or via any other effective means.

Specific embodiments of the invention will now be demonstrated by reference to the following examples. It should be understood that these examples are disclosed solely by way of illustrating the invention and should not be taken in any way to limit the scope of the present invention.

Definitions
THF—Tetrahydrofuran
DMF—Dimethylformamide
Type of Equipment and Calibration of Analytical Equipment:
X-ray powder diffraction (XRPD): Equipment: Bruker D8 Advance. Reflection, Cu radiation
FT-IR in Nujol, Instrument: Bruker VERTEX 70
Single crystal structure: Equipment: Bruker AXS, CuK$_\alpha$ radiation
FT-Raman: Bruker RFS100-S, laser power 50 mW (1004 nm)

Example 1

4-Amino-5-fluoro-3-[5-(4-methylpiperazin-1-yl)-1H-benzimidazol-2-yl]quinolin-2(1H)-one lactate anhydrous form II By equilibration by stirring of slurry of the anhydrous form A and preferably excess of lactic acid in organic solvents such as ethanol, or ethanol 98:2 (v/v) acetonitrile, isopropanol, anhydrous form A transforms into anhydrous form II.

By equilibration of the monohydrate form B preferably in presence of an excess of lactic acid, the anhydrous form II is obtained in ethanol or isopropanol or acetonitrile.

Titration of 4-amino-5-fluoro-3-[5-(4-methylpiperazin-1-yl)-1H-benzimidazol-2-yl]quinolin-2(1H)-one by perchloric acid and titration of the lactic acid shows the stoichiometry 1:1 of the base and lactic acid. Thermogravimetry water <0.5%, purity HPLC>99.5%.

Heating of the anhydrous form II transforms it into the anhydrous form A as observed by X-ray heating cell at about 160° C. By differential scanning calorimetry (DSC) the transformation occurs with endotherm which shows that anhydrous A and anhydrous II are in enantiotropic relationship. This is confirmed by the heat of solution in water at 25° C., Form B is more endothermic than form A: 9.2 kJ/mol compared to 4.6 KJ/mol.

In ethanol/water mixtures in slurry anhydrous form II may transform into the monohydrate form B (low amounts water) or into the hemi-pentahydrate (higher amounts of water).

Heating the monohydrate form B at 100-140° C. anhydrous form A or anhydrous form II or mixtures are obtained.
Solubility of Anhydrous Form II Compared to Anhydrous Form A

| Solvent | Ethanol | Acetone | Isopropanol | Butanol | Water |
|---|---|---|---|---|---|
| Anhydrous form II | 0.71 mg/ml | 0.51 mg/ml | 0.08 mg/ml | 0.34 mg/ml | 68 mg/ml |
| Anhydrous form A | 0.84 mg/ml | 0.84 mg/ml | 0.16 mg/ml | 0.95 mg/ml | 107 mg/ml |

Example of Preparation

A slurry of 7 g 4-amino-5-fluoro-3-[5-(4-methylpiperazin-1-yl)-1H-benzimidazol-2-yl]quinolin-2(1H)-one lactate monohydrate form B in 70 ml ethanol absolute is equilibrated by stirring at 25° C. during 24 h. The solid filtered is dried and consists of 4-amino-5-fluoro-3-[5-(4-methylpiperazin-1-yl)-1H-benzimidazol-2-yl]quinolin-2(1H)-one lactate salt anhydrous form II.

The single crystal X-ray structure is determined and confirmed the X-ray powder diffraction.

Example 2

4-Amino-5-fluoro-3-[5-(4-methylpiperazin-1-yl)-1H-benzimidazol-2-yl]quinolin-2(1H)-one lactate hemi-pentahydrate By crystallization in ethanol/water mixture with high content of water, the hemi-pentahydrate is obtained.

By equilibration of the anhydrous form A, a complete transformation into the hemi-pentahydrate is observed in mixtures ethanol/water 80:20 until 60:40 at 25 to 50° C. or in mixtures ethanol/water/THF or in mixture acetone/water 90:10. Loss on drying by thermogravimetry before the lost of lactic acid: 8.6% (theory for hemi-pentahydrate 8.5%).

Titration by perchloric acid: 100.0%, titration of lactic acid on anhydrous basis 18.9%, water: 8.1-8.6%, purity by HPLC>99.5%.

The hemi-pentahydrate has a more endothermic heat of solution in water at 25° C. compared to anhydrous forms A or B: 30 kJ/mol.

By heating the hemi-pentahydrate transforms into a new form, possibly an hemi-hydrate (TG: 1.39%) as observed by X-ray heating cell at about 100° C. By DSC the transformation occurs followed by the melting and recrystallization at 130-140° C. into the anhydrous form A. Same observations by heating X-ray experiment. By equilibration of slurries of the hemi-pentahydrate in organic solvents such as ethanol, acetone. THF, the hemi-pentahydrate transforms into anhydrous form A or mixture of anhydrous form A and monohydrate form B.

Solubility of hemi-pentahydrate at 25° C.: water: 6.2 mg/ml; HCl 0.1N: 55 mg/ml, ethanol: 2 mg/ml.

Example of Preparation 5 g of 4-amino-5-fluoro-3-[5-(4-methylpiperazin-1-yl)-1H-benzimidazol-2-yl]quinolin-2(1H)-one free base are dissolved in a mixture of 27.6 g of ethanol and 2.4 g of water. 0.5 g of lactic acid are added and the solution is kept under stirring at 50° C. for 40-48 hours. A suspension is obtained and the solid filtered is dried and consists of 4-amino-5-fluoro-3-[5-(4-methylpiperazin-1-yl)-1H-benzimidazol-2-yl]quinolin-2(1H)-one lactate salt hemi-pentahydrate.

The single crystal X-ray structure is determined and confirmed by X-ray powder diffraction (see Table 1).

Example 3

4-Amino-5-fluoro-3-[5-(4-methylpiperazin-1-yl)-1H-benzimidazol-2-yl]quinolin-2(1H)-one lactate methanol-solvate By equilibration of slurry of the monohydrate or anhydrous form A or anhydrous form II in methanol, a complete transformation into the solvate is observed at 25° C.

The single crystal X-ray structure is determined and confirmed by X-ray powder diffraction (see Table 1).

Example 4

4-Amino-5-fluoro-3-[5-(4-methylpiperazin-1-yl)-1H-benzimidazol-2-yl]quinolin-2(1H)-one lactate DMF-solvate By equilibration of slurry of the monohydrate or anhydrous form A in DMF, a transformation into the solvate is observed at 25° C.: example the monohydrate is completely transformed in the solvate: TG: 15.5% (theory: 13.1%).

The single crystal X-ray structure is determined and confirmed by X-ray powder diffraction (see Table 1).

TABLE 1

Crystallographic Data

| | Anhydrous Form II | Hemi-pentahydrate | Methanol-Solvate | DMF-Solvate |
|---|---|---|---|---|
| Empirical formula | C21 H22 F N6 O, C3 H5 O3c | C24 H32 F N6 O6.50 | C25 H31 F N6 O5 | C28 H 34 F N7 O5 |
| Formula weight | 482.52 g · mol−1 | 527.56 g · mol−1 | 514.52 g · mol−1 | 555.61 g · mol−1 |
| Temperature | 100(2) K | 293(2) K | 100 (2) K | 100 (2) K |
| Wavelength | 1.54178 Å | 1.54178 Å | 1.54178 Å | 1.54178 Å |
| Crystal system | Monoclinic | Monoclinic | Monoclinic | Triclinic |
| Space group | P21/n | C2/c | P21/n | P1 |
| Unit cell dimensions | a = 13.310(6) Å<br>b = 7.816(3) Å<br>c = 21.612(9) Å<br>alpha = 97.62(3)°<br>beta = 90°<br>gama = 90° | a = 13.687(2) Å<br>b = 13.465(2) Å<br>c = 27.081(4) Å<br>alpha = 101.626(8)°<br>beta = 90°<br>gamma = 90° | a = 16.326 (6) Å<br>b = 8.093 (3) Å<br>c = 18.860 (6) Å<br>alpha = 100.886 (2)°<br>beta = 90°<br>gamma = 90° | a = 7.963 (2) Å<br>b = 9.486 (2) Å<br>c = 18.670 (4) Å<br>alpha = 99.943 (1)°<br>beta = 94.9432 (1)°<br>gamma = 108.994 (1) |
| Volume | 2229(16) Å$^3$ | 4888 (12) Å$^3$ | 2447 (15) Å$^3$ | 1297 (5) Å$^3$ |
| Z | 4 | 8 | 4 | 2 |
| Density (theoretical) | 1.438 g · cm−3 | 1.434 g · cm−3 | 1.310 g · cm−3 | 1.422 g · cm−3 |

Figure 5A:
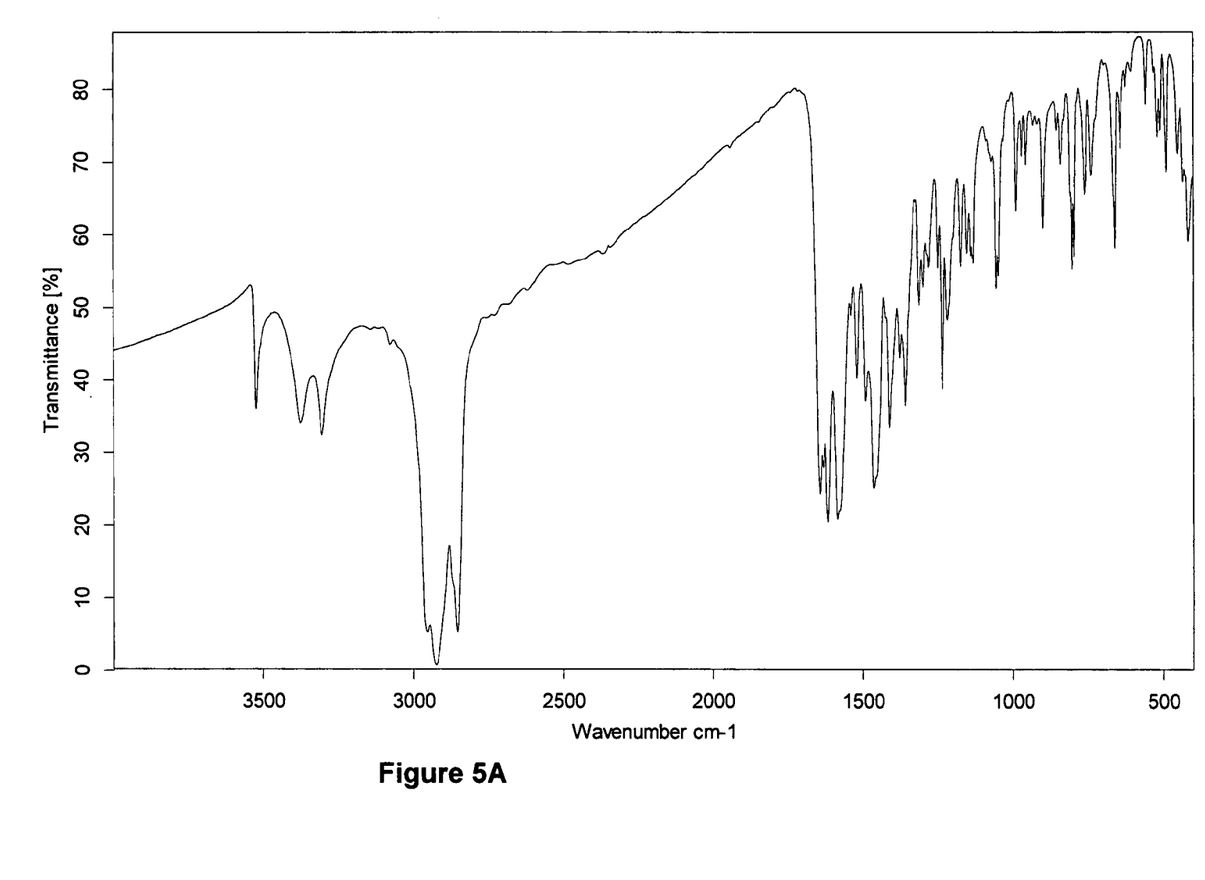
FIG. 5A shows the FT-IR spectra for the new anhydrous form of the lactic acid salt of 4-amino-5-fluoro-3-[5-(4-methylpiperazin-1-yl)-1H-benzimidazol-2-yl]quinolin-2(1H)-one.
Figure 5B:
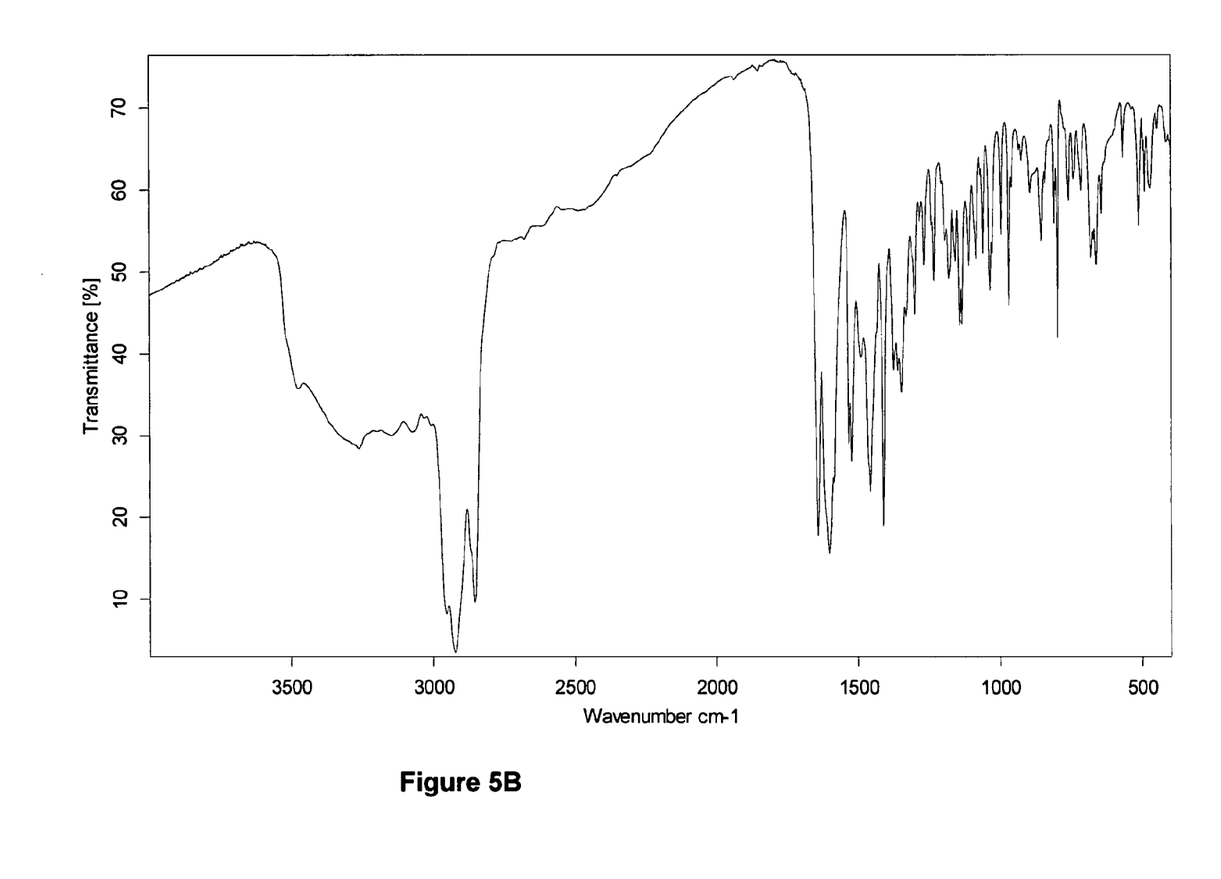
FIG. 5B shows the FT-IR spectra for the hemi-pentahydrate form of the lactic acid salt of 4-amino-5-fluoro-3-[5-(4-methylpiperazin-1-yl)-1H-benzimidazol-2-yl]quinolin-2(1H)-one.
Figure 5C:
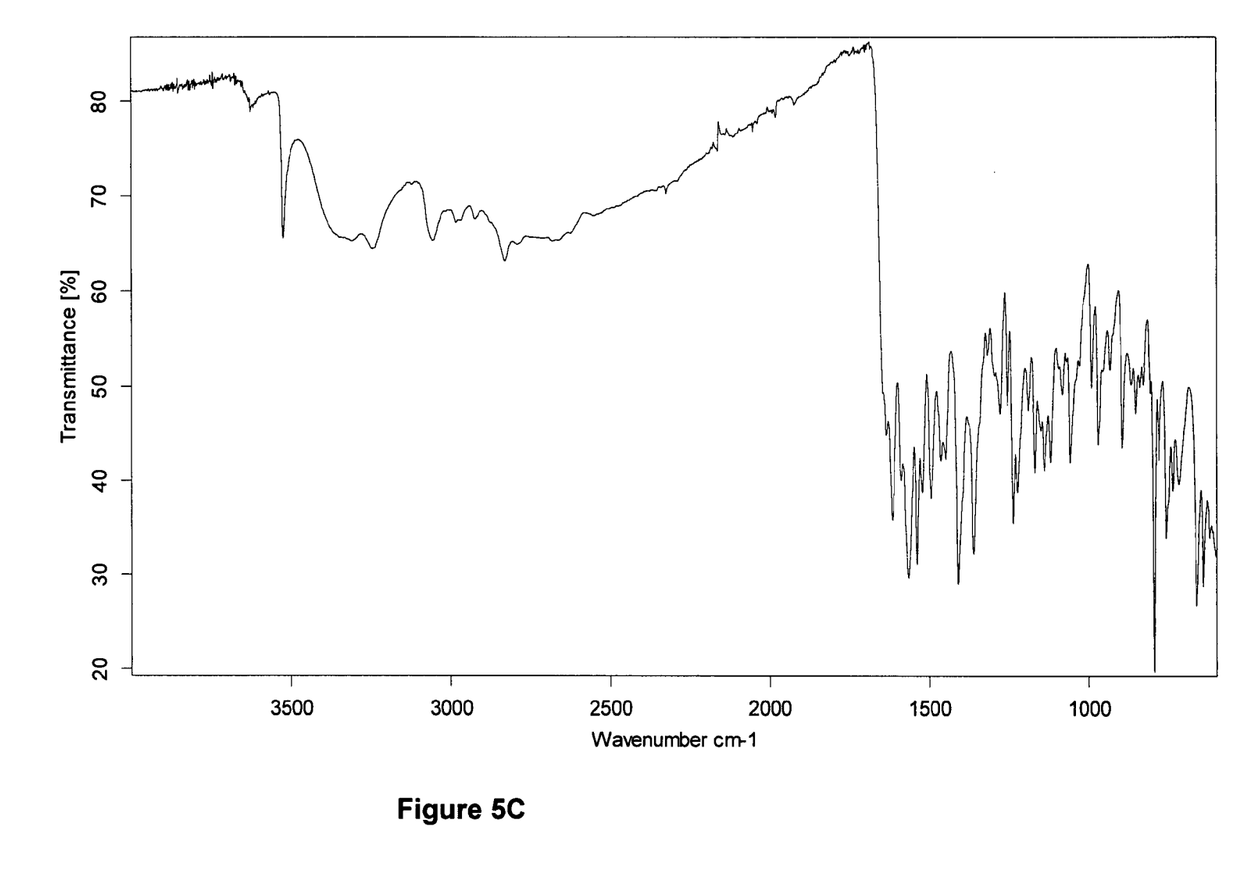
FIG. 5C shows the FT-IR spectra for the methanol-solvate form of the lactic acid salt of 4-amino-5-fluoro-3-[5-(4-methylpiperazin-1-yl)-1H-benzimidazol-2-yl]quinolin-2(1H)-one.

FT-IR spectra absorption bands of FIGS. 5A, 5B and 5C are found in Table 2.

TABLE 2

| Form | Characteristic absorption bands [cm$^{-1}$] |
|---|---|
| Anhydrous A | 3507, 3417, 3278, 2925*, 2855*, 1645, 1630, 1604, 1543, 1525, 1459*, 1411, 1378*, 1353, 1236, 1218, 1169, 1141, 1088, 1062, 1054, 1039, 997, 898, 804, 665, 545 |
| Anhydrous B (or anhydrous II) | 3524, 3376, 3305, 2924*, 2854*, 1644, 1617, 1585, 1520, 1464*, 1411, 1360, 1313, 1235, 1218, 1174, 1056, 989, 957, 899, 802, 796, 760, 660, 558, 489 |
| Hemi-pentahydrate | ~3265, 1642, 1601, 1523, 1490, 1458*, 1411, 1348, 1299, 1267, 1232, 1179, 1156, 1133, 1084, 1059, 1034, 995, 969, 853, 796, 758, 741, 713, 660, 566, 511, 490 |
| Solvate methanol | 3524, 3244, 2831, 1615, 1564, 1538, 1494, 1462, 1409, 1360, 1277, 1254, 1236, 1168, 1138, 1118, 1057, 990, 969, 894, 852, 796, 758, 663, 642 |

Figure 6A:
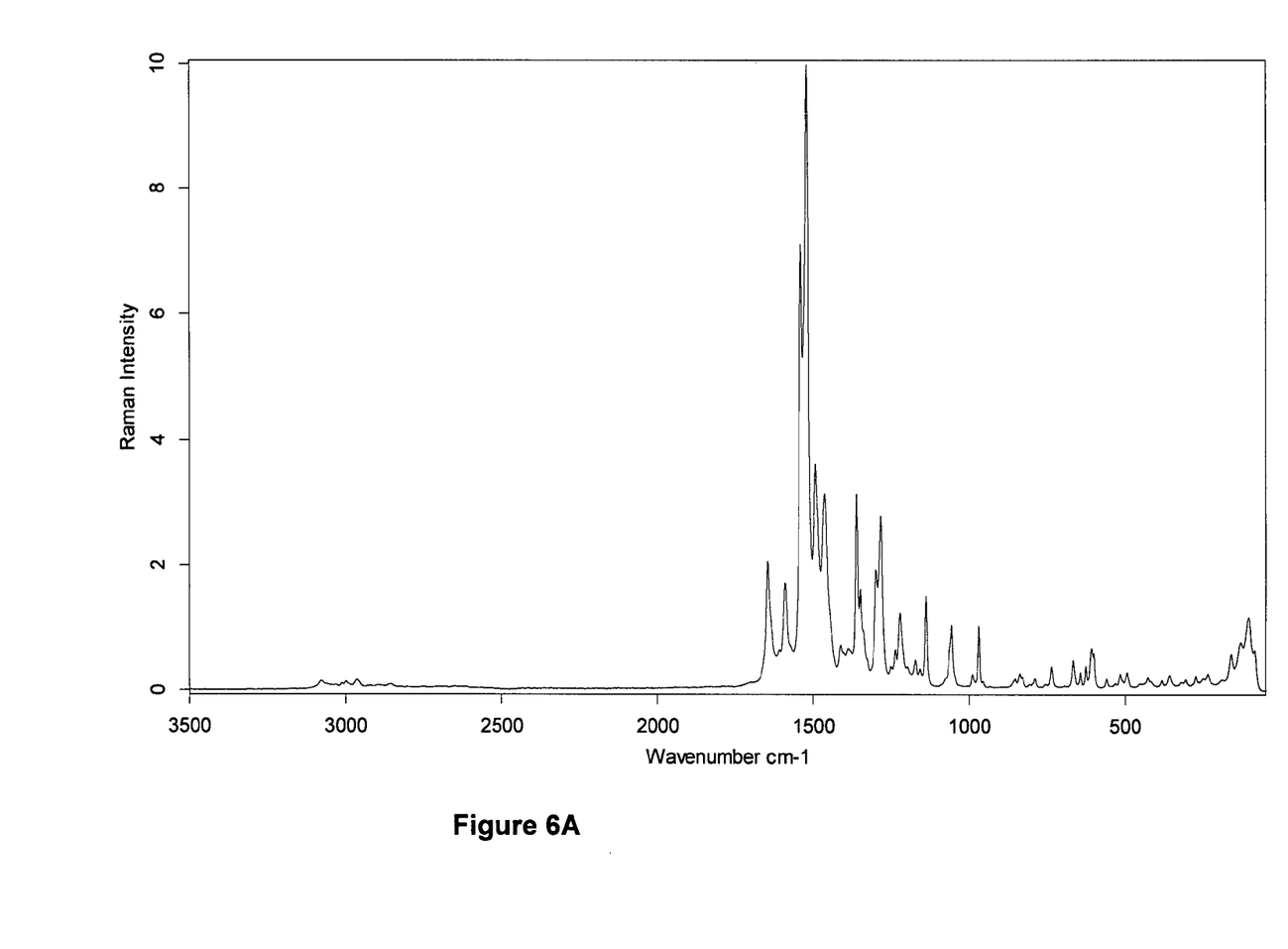
FIG. 6A shows the Raman spectra for the new anhydrous form of the lactic acid salt of 4-amino-5-fluoro-3-[5-(4-methylpiperazin-1-yl)-1H-benzimidazol-2-yl]quinolin-2(1H)-one.
Figure 6B:
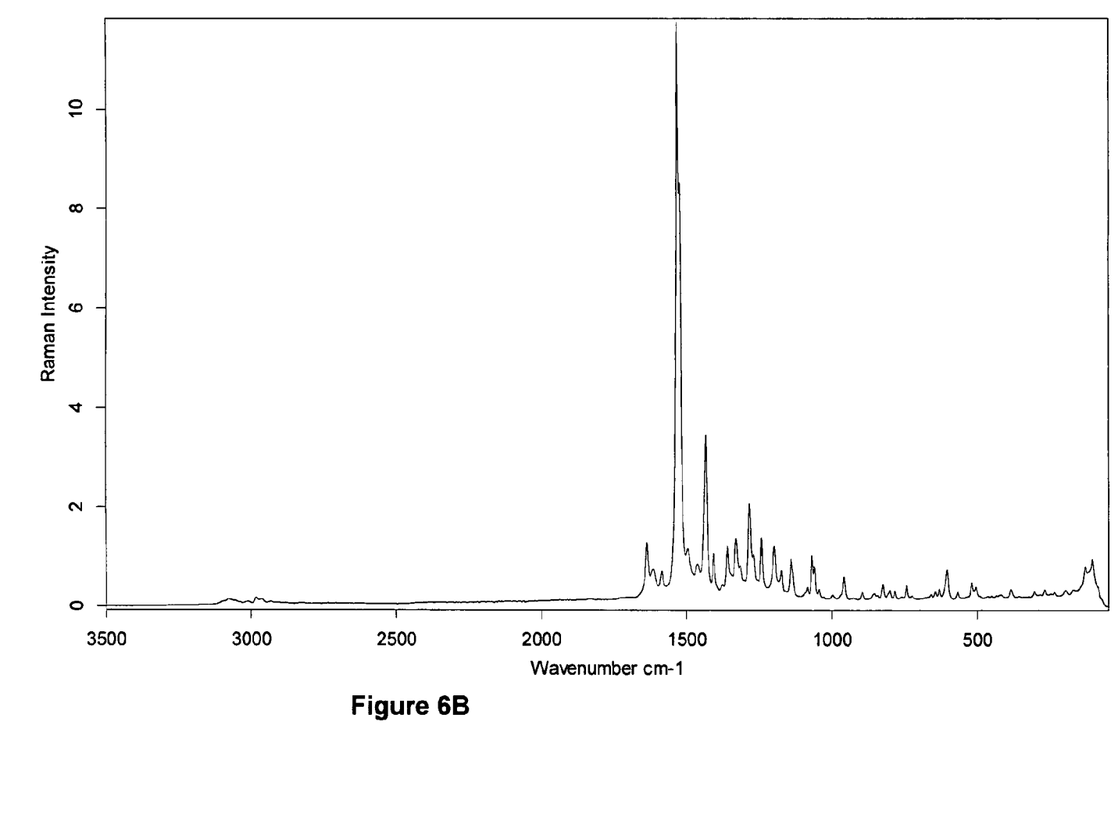
FIG. 6B shows the Raman spectra for the hemi-pentahydrate form of the lactic acid salt of 4-amino-5-fluoro-3-[5-(4-methylpiperazin-1-yl)-1H-benzimidazol-2-yl]quinolin-2(1H)-one.
Figure 6C:
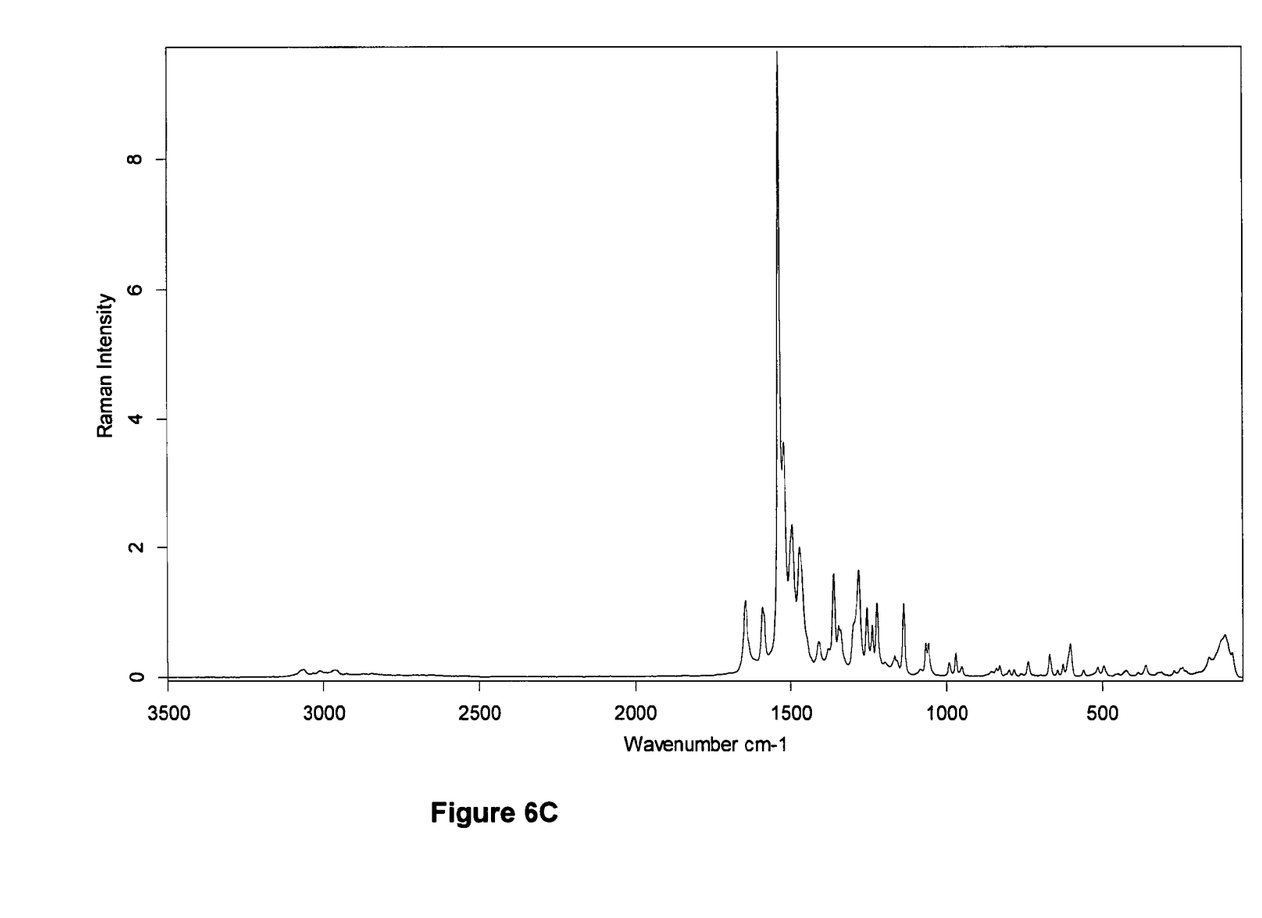
FIG. 6C shows the Raman spectra for the methanol-solvate form of the lactic acid salt of 4-amino-5-fluoro-3-[5-(4-methylpiperazin-1-yl)-1H-benzimidazol-2-yl]quinolin-2(1H)-one.

Raman spectra adsorption bands of FIGS. 6A, 6B, 6C are found in Table 3.

TABLE 3

| Form | Characteristic absorption bands [cm$^{-1}$] |
|---|---|
| Anhydrous A | 3061, 2992, 2956, 1641, 1589, 1543, 1527, 1489, 1464, 1375, 1282, 1239, 1219, 1168, 1135, 1054, 974, 789, 739, 664, 609, 512, 501, 493, 370, 257, 230, 150, 129, |
| Anhydrous II | 3079, 2963, 1645, 1589, 1540, 1520, 1492, 1464, 1412, 1361, 1348, 1298, 1282, 1237, 1138, 1056, 970, 736, 667, 608, 160, 105 |
| Hemi-pentahydrate | 3078, 2983, 1637, 1616, 1585, 1533, 1495, 1434, 1407, 1360, 1330, 1283, 1243, 1198, 1141, 1067, 959, 823, 743, 603, 519, 385, 130, 107 |

While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims. All patent applications, patents, and other publications cited herein are incorporated by reference in their entirety.

What is claimed is:

1. A substantially pure crystalline anhydrous form of 4-amino-5-fluoro-3-[5-(4-methylpiperazin-1-yl)-1H-benzimidazol-2-yl]quinolin-2(1H)-one lactic acid salt characterized by an x-ray powder diffraction pattern that shows a characteristic maxima at 8.2, 18.5 degrees, 2 theta.

2. A substantially pure crystalline anhydrous form II of 4-amino-5-fluoro-3-[5-(4-methylpiperazin-1-yl)-1H-benzimidazol-2-yl]quinolin-2(1H)-one lactic acid salt characterized by the x-ray powder diffraction pattern shown in FIG. 1.

3. The substantially pure crystalline form of claim 1, wherein the x-ray powder diffraction pattern shows characteristic maxima at 8.2, 11.8, 12.9, 13.8, 14.7, 16.6, 18.5, 20.3, 23.5 degrees, 2 theta.

4. A pharmaceutical composition comprising:
   (a) a therapeutically effective amount of a crystalline form of claim 1; and
   (b) at least one pharmaceutically acceptable carrier, diluent, vehicle or excipient.

5. A method of treating a disease which responds to an inhibition of VEGFR2 and FGFR3 activity comprising the step of administering to a subject in need of such treatment a therapeutically effective amount of a crystalline form of claim 1, wherein said disease is selected from the group consisting of prostate cancer, colorectal cancer, breast cancer, multiple myeloma, pancreatic cancer, small cell carcinoma, acute myelogenous leukemia, chronic myelogenous leukemia, myelo-proliferative disease, non-small cell leukemia, small cell leukemia, chronic lymphoid leukemia, sarcoma, melanoma, lymphoma, thyroid cancer, neuroendocrine cancer, renal cell cancer, gastric cancer, gastrointestinal stromal cancer, glioma, brain cancer, bladder cancer and cholangiocarcinoma.

6. A method of treating a disease which responds to an inhibition of VEGFR2 and FGFR3 activity comprising the step of administering to a subject in need of such treatment a therapeutically effective amount of a crystalline form of claim 2, wherein said disease is selected from the group consisting of prostate cancer, colorectal cancer, breast cancer, multiple myeloma, pancreatic cancer, small cell carcinoma, acute myelogenous leukemia, chronic myelogenous leukemia, myelo-proliferative disease, non-small cell leukemia, small cell leukemia, chronic lymphoid leukemia, sarcoma, melanoma, lymphoma, thyroid cancer, neuroendocrine cancer, renal cell cancer, gastric cancer, gastrointestinal stromal cancer, glioma, brain cancer, bladder cancer and cholangiocarcinoma.

7. A method of treating a disease which responds to an inhibition of VEGFR2 and FGFR3 activity comprising the step of administering to a subject in need of such treatment a therapeutically effective amount of a crystalline form of claim 3, wherein said disease is selected from the group consisting of prostate cancer, colorectal cancer, breast cancer, multiple myeloma, pancreatic cancer, small cell carcinoma, acute myelogenous leukemia, chronic myelogenous leukemia, myelo-proliferative disease, non-small cell leukemia, small cell leukemia, chronic lymphoid leukemia, sarcoma, melanoma, lymphoma, thyroid cancer, neuroendocrine cancer, renal cell cancer, gastric cancer, gastrointestinal stromal cancer, glioma, brain cancer, bladder cancer and cholangiocarcinoma.

* * * * *